United States Patent [19]

Persson

[11] Patent Number: Plant 5,817

[45] Date of Patent: Dec. 2, 1986

[54] CHRYSANTHEMUM PLANT NAMED YELLOW DRAMATIC

[76] Inventor: Kjell-Ake Persson, Vaartoepets Handelstraegaard Kjoepingegatan 70, 23100 Trelleborg, Sweden

[21] Appl. No.: 681,481

[22] Filed: Dec. 13, 1984

[51] Int. Cl.[4] ..... A01H 5/00

[52] U.S. Cl. ..... Plt./74

[58] Field of Search ..... Plt./74

*Primary Examiner*—R. E. Bagwill

*Attorney, Agent, or Firm*—Schwartz, Jeffery, Schwaab, Mack, Blumenthal & Evans

[57] ABSTRACT

A Chrysanthemum plant named Yellow Dramatic, discovered as a spontaneous mutation within a flowering block of Dramatic, disclosed in U.S. Plant Pat. No. 3,189. Yellow Dramatic is particularly characterized as to uniqueness by the combined characteristics of flat capitulum form; daisy capitulum type; yellow tinged orange ray floret color; diameter across face of capitulum ranging from 6 to 9 cm. at maturity; uniform nine week photoperiodic flowering response to short days; medium plant height when grown single stem; 8 to 12 cm. peduncles on open, normally terminal sprays; and 13° C. minimum temperature tolerance for initiation and development of flowering buds. Development and retention of the orange carotene as expressed by Dramatic is significantly reduced in all stages of maturation and under all environments tested to date. Yellow Dramatic is similar to Dramatic in all other traits.

3 Drawing Figures

The present invention comprises a new and distinct cultivar of *Chrysanthemum morifolium*, Ramat., named Yellow Dramatic.

Yellow Dramatic was discovered as a spontaneous mutation within a flowering block of Dramatic (U.S. Plant Pat. No. 3,189) and selected by Kjell-Ake Persson on Apr. 4, 1979 in a greenhouse in Kjoepingegatan 70, Sweden.

The first act of asexual reproduction of Yellow Dramatic was accomplished when vegetative cuttings were taken from the initial selection of Aug. 5, 1979 in a controlled environment in Kjoepingegatan 70, Sweden by Kjell-Ake Persson.

Horticultural examination of selected units initiated Oct. 15, 1980 has demonstrated that the combination of characteristics as herein disclosed for Yellow Dramatic are firmly fixed and are retained through successive generations of asexual reproduction.

Yellow Dramatic has not been observed under all possible environmental conditions. The phenotype may vary significantly with variations in environments such as temperature, light intensity and day length. The following observations, measurements and comparisons describe plants grown in Salinas, Calif. and Leamington, Ontario, Canada under greenhouse conditions which approximate those generally used in commercial practice.

The following traits have been repeatedly observed and are determined to be basic characteristics of Yellow Dramatic which in combination distinguish this Chrysanthemum as a new and distinct cultivar:

(1) Flat capitulum form.

(2) Daisy capitulum type.

(3) Yellow tinged orange floret color.

(4) Diameter across face of capitulum ranging from 6 to 9 cm. at maturity.

(5) Uniform nine week photoperiodic flowering response to short days.

(6) Short peduncle length, ranging from 8 to 12 cm.

(7) Medium plant height requiring 2 to 3 long day weeks prior to short days to attain a flowered plant height of 80 to 90 cm. for April through October flowerings with single stem procedure.

(8) Low temperature tolerance of 13° C. for initiation and development when grown in single stem cut spary programs with a continuous dark period of 13 hours.

The accompanying photographic drawings show typical inflorescence and leaf characteristics of Yellow Dramatic, with the colors being as nearly true as possible with illustrations of this type.

Sheet 1 is a color photograph of Yellow Dramatic grown as a single stem cut spray.

Sheet 2 is a black and white photograph of three views of the inflorescence of Yellow Dramatic.

Sheet 3 is a black and white photograph showing the upper and under surfaces of leaves of Yellow Dramatic at three stages of development (mature, intermediate and immature).

Of the many commercial cultivars known to the present inventor, the most similar in comparison to Yellow Dramatic is Dramatic disclosed in U.S. Plant Pat. No. 3,189.

Reference is made to attached Chart A which compares certain characteristics of Yellow Dramatic to those same characteristics of Dramatic. Yellow Dramatic is similar to Dramatic in all traits except color. The development and expression of the orange carotene by Dramatic is significantly reduced in Yellow Dramatic. The color mutation discovered closely approximates yellow. In comparison Dramatic is a golden bronze.

In the following description, color references are made to The Royal Horticultural Society Colour Chart. The color values were determined between 10:00 A.M. and 10:15 A.M. on June 29, 1984 under 380 foot-candle light intensity at Salinas, Calif.

Classification:

*Botanical.*—*Chrysanthemum morifolium,* Ramat., cv Yellow Dramatic.

*Commercial.*—Daisy cut spray mum.

I. INFLORESCENCE

A. Capitulum:

*Form.*—Flat.

*Type.*—Daisy.

*Diameter across face.*—6 to 9 cm.

B. Corolla of ray florets:

*Color (general tonality from a distance of three meters).*—Yellow tinged orange.

*Color (upper surface).*—9A tinged 14A.

*Color (under surface).*—6A, 6B.

*Shape.*—Keeled, tapering to a rounded point.

C. Corolla of disc florets:

*Color (mature).*—2B.

*Color (immature).*—145A.

D. Reproductive organs:

*Androecium.*—Present disc florets only; moderate pollen.

*Gynoecium.*—Present both ray and disc florets.

II. PLANT

A. General appearance:

*Height.*—Medium; 56 to 66 cm., as a single stem flowering plant from a rooted cutting, with no long days from April through October flowerings maintaining a minimum nightly 13 hour continuous dark period.

B. Foliage:

*Color (upper surface).*—147A.

*Color (under surface).*—147B.

*Shape.*—Deeply lobed; deeply serrated.

CHART A

COMPARISON OF YELLOW DRAMATIC AND DRAMATIC

| CULTIVAR | RAY FLORET COLOR | CAPITULUM FORM AND TYPE | SPRAY FORMATION |
|---|---|---|---|
| YELLOW DRAMATIC | YELLOW TINGED ORANGE | FLAT DAISY | TERMINAL AND COMPOUND |
| DRAMATIC | GOLDEN BRONZE | FLAT DAISY | TERMINAL AND COMPOUND |

CHART A-continued

COMPARISON OF YELLOW DRAMATIC AND DRAMATIC

| CULTIVAR | DIAMETER ACROSS FACE OF CAPITULUM | PLANT HEIGHT | FLOWERING RESPONSE PERIOD | LOW TEMPERATURE TOLERANCE |
|---|---|---|---|---|
| YELLOW DRAMATIC | 6 to 9 cm. | MEDIUM 56 to 66 cm. | NINE WEEKS | 13° C. |
| DRAMATIC | 6 to 9 cm. | MEDIUM 56 to 66 cm. | NINE WEEKS | 13° C. |

COMPARISONS MADE OF PLANTS GROWN AS SINGLE STEM CUT SPRAY MUMS WITH NO LONG DAYS IN SALINAS, CALIFORNIA

I claim:

1. A new and distinct plant of *Chrysanthemum morifolium,* Ramat., named Yellow Dramatic, as described and illustrated, and particularly characterized as to uniqueness by the combined characteristics of flat capitulum form; daisy capitulum type; yellow tinged orange ray floret color; diameter across face of capitulum ranging from 6 to 9 cm. at maturity; uniform nine week flowering response; medium plant height when grown single stem; 8 to 12 cm. peduncles on open, normally terminal sprays; 13° C. minimum temperature tolerance for initiation and development of flowering buds; and significantly reduced development of the orange carotene as expressed by the parent cultivar Dramatic, in all stages of maturation and all environments tested to date.

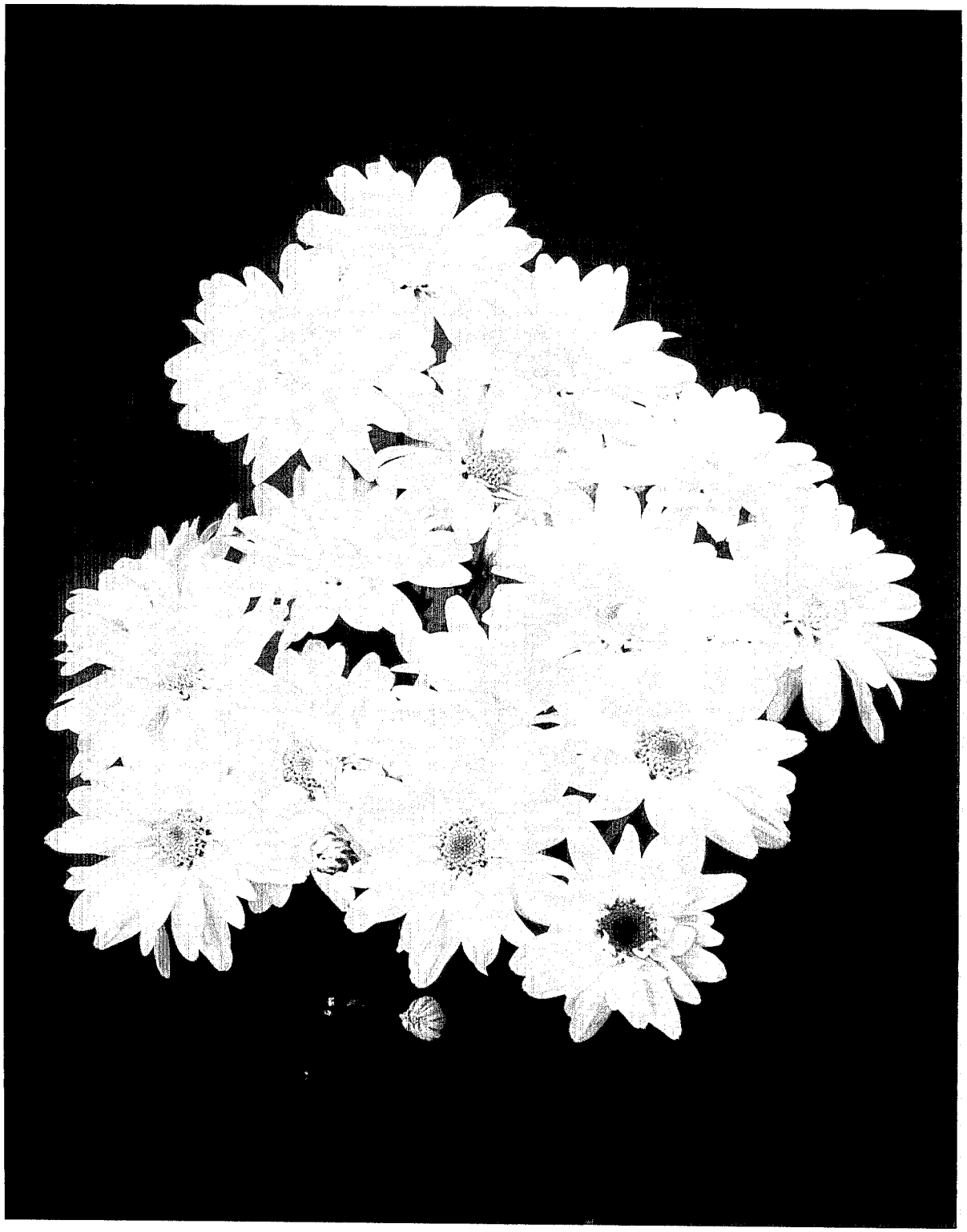

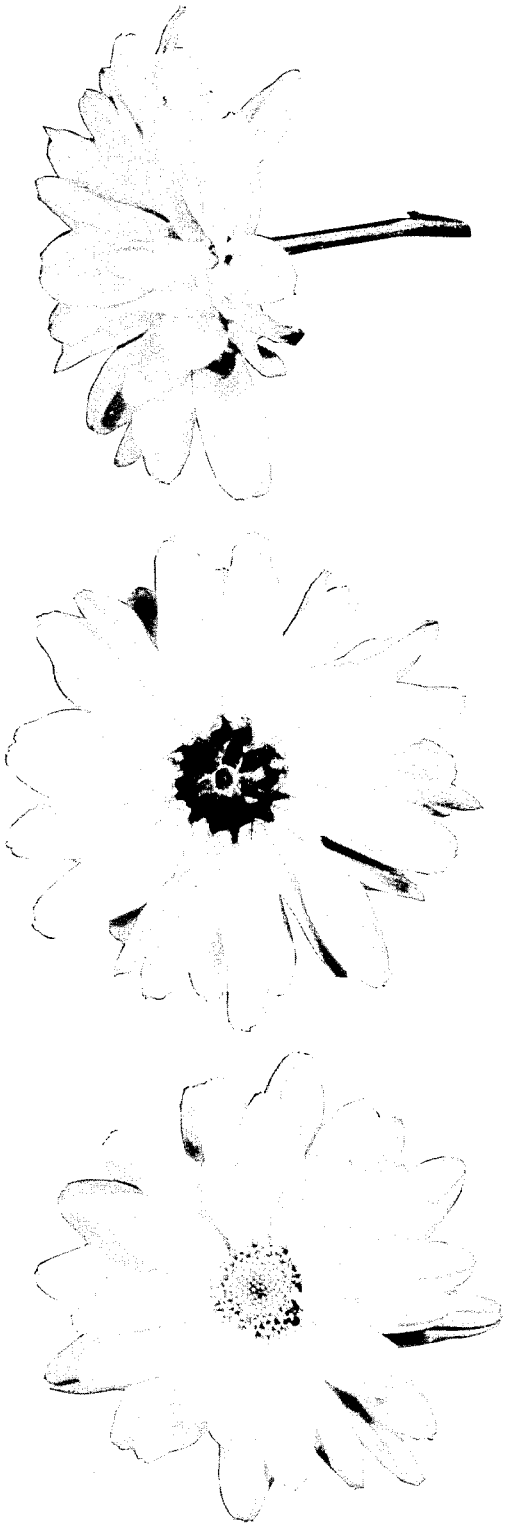

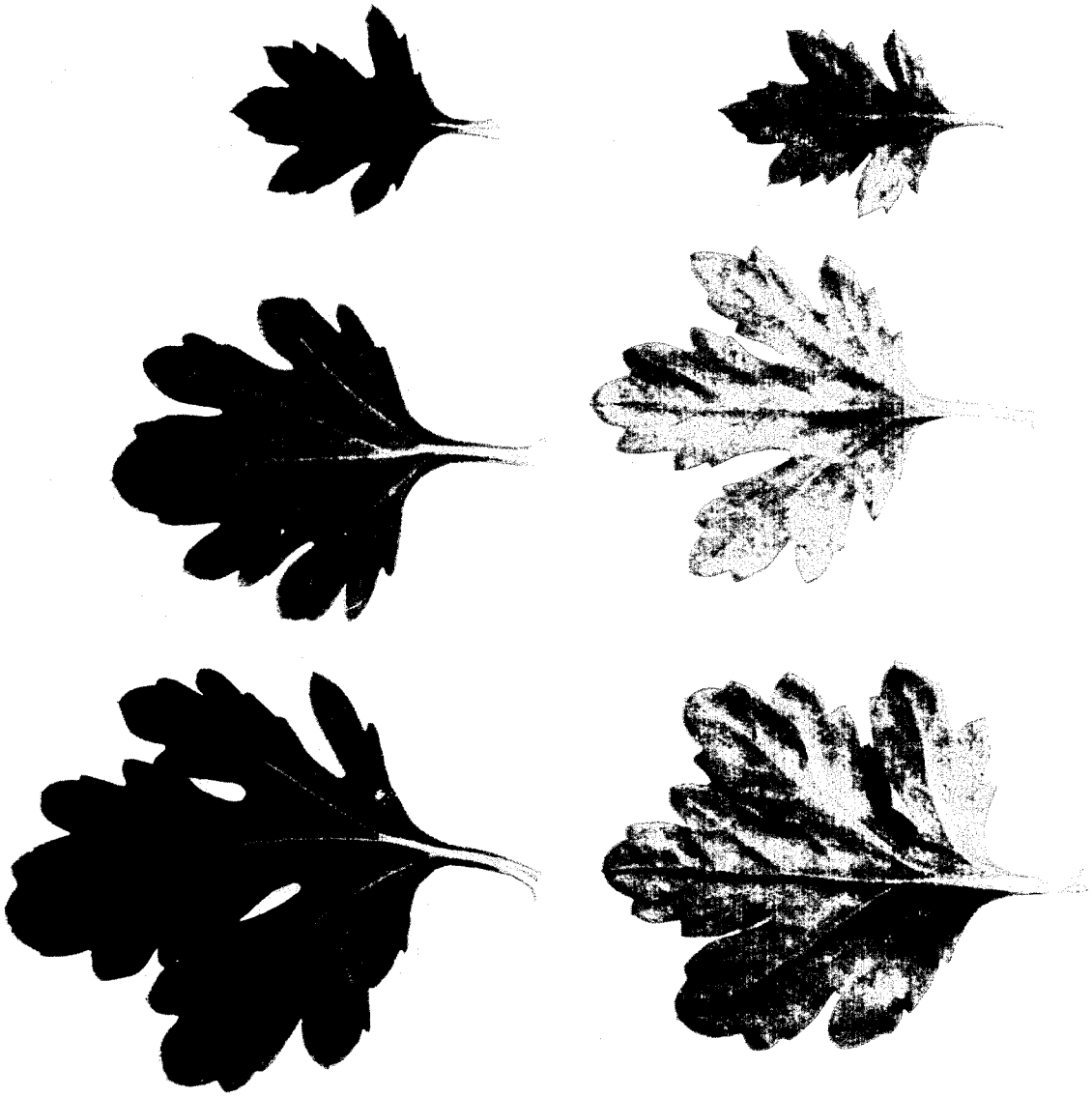

* * * * *